US011324577B2

(12) United States Patent
Stopka et al.

(10) Patent No.: US 11,324,577 B2
(45) Date of Patent: May 10, 2022

(54) DENTAL TOOL HOLDER (71) Applicant: Nordent Manufacturing, Elk Grove Village, IL (US)

(72) Inventors: Tom Stopka, St. Charles, IL (US); Tim Irwin, Orland Park, IL (US); Richard Martin, Elk Grove Village, IL (US)

(73) Assignee: Nordent Manufacturing, Elk Grove Village, IL (US)

( * ) Notice: Subject to any disclaimer, the term of this patent is extended or adjusted under 35 U.S.C. 154(b) by 141 days.

(21) Appl. No.: 16/804,988

(22) Filed: Feb. 28, 2020

(65) Prior Publication Data
US 2021/0267736 A1 Sep. 2, 2021

(51) Int. Cl.
- *A61C 19/00* (2006.01)
- *A61C 19/02* (2006.01)
- *A61B 50/33* (2016.01)

(52) U.S. Cl.
CPC .............. *A61C 19/02* (2013.01); *A61B 50/33* (2016.02); *A61C 19/002* (2013.01)

(58) Field of Classification Search
CPC ......... A61C 19/02; A61C 19/002; A61L 2/26; A61L 2202/24; A61B 50/20; A61B 50/33
USPC ......................................................... 206/369
See application file for complete search history.

(56) References Cited

U.S. PATENT DOCUMENTS

| | | | | |
|---|---|---|---|---|
| 5,084,251 A | * | 1/1992 | Thomas | A61C 19/02 206/557 |
| 6,193,932 B1 | * | 2/2001 | Wu | A61L 2/07 206/210 |
| 6,244,447 B1 | * | 6/2001 | Frieze | A61L 2/07 206/370 |

OTHER PUBLICATIONS

Zirc, "E-Z Jett Cassette Feet (2pk) Product Code: 50R925", web page https://www.zirc.com/products/instrument-holders/e-z-jett-cassette-feet-2pk, Zirc, Buffalo, MN.

\* cited by examiner

*Primary Examiner* — King M Chu
(74) *Attorney, Agent, or Firm* — McGarry Bair PC (57) ABSTRACT

An apparatus and method for a dental tool holder for use with a cassette assembly for cleaning and preparing dental tools for use. The dental tool holder includes a body with a set of openings. A set of slits extend through the exterior of the body to the openings for the insertion of tools. Opposite of the openings, a valley can be formed in the body at each slit. Additionally, slots can be provided between each set of one slit and one opening.

13 Claims, 7 Drawing Sheets

DENTAL TOOL HOLDER

BACKGROUND OF THE INVENTION

Dental cassettes are used in holding, storing, sterilizing, sanitizing, using, and cleaning dental tools, among other things. These cassettes are often metal cases, having a plurality of openings or holes to permit steam, disinfectant, or cleaning solution to enter the interior of the cassette to clean and sanitize the dental tools. Within the cassettes are tool holders, often made of silicone, rubber, polymers, or other material for supporting the tools within the cassette in an organized or arranged manner. However, the capabilities of the cassette, such as storage or cleaning, are limited by current tool holder design. Such limitations result in inefficiencies, such as increased cleaning time or cycles, as well as a limited number of tools being cleaned or stored within a particular cassette. When the cassette and tools are utilized, a dentist or other professional are limited to those tools contained within the cassette, unless the dentist or professional utilizes multiple cassettes, or takes tools from another cassette.

BRIEF DESCRIPTION OF THE INVENTION

In one aspect, the disclosure relates to a tool holder for holding dental instruments, the tool holder comprising: a body including a front face, a rear face, and a top surface; at least one opening extending through the body from the front face to the rear face; at least one slit extending into the body from the top surface and terminating at the opening.

In another aspect, the disclosure relates to a tool holder assembly for holding dental instruments within a dental cassette, the tool holder assembly comprising: a first dental tool holder and a second dental tool holder, each including: a body with a set of openings, with a set of slits, complementary to the set of openings, extending through the body to the set of openings.

In yet another aspect, the disclosure relates to a method of preparing dental tools for cleaning in a cassette, the method comprising: inserting a set of tools, through a set of slits, into a complementary set of openings in a dental tool holder.

DETAILED DESCRIPTION OF THE INVENTION

Aspects of the disclosure described herein are directed to a dental tool holder. The dental tool holder includes a set of openings with a set of slits extending from the exterior of the dental tool holder to the set of openings. The dental tool holder (or pair thereof) secures the dental tools within the holder, permitting dental tools to be carried in a dental tool holder on both the top and bottom of a carrying cassette, while traditional cassettes require an element or component to hold the dental tools in place, such as the insert 32 of FIG. 1. The additional set of dental tools increases cleaning capacity, as well as improved customization for dental tool sets contained within a cassette. In use, dental tools can be inserted into the openings through the slits, with the dental tool holder then holding a first set of tools. Then, an additional second set of tools can be carried in a separate dental tool holder, such as one secured on the opposing half of the cassette.

Aspects of the disclosure described herein are directed to a holder, a system for holding, and a method for holding dental tools within a dental cassette. While the disclosure herein is directed to a cassette for holding dental tools, it should be appreciated that the cassette need not be limited to the dental industry, but can have applicability in any suitable industry where cleaning and sanitizing tools may be desirable, such as the medical industry in one non-limiting example.

As used herein, the term "set" when referring to a number of elements can include any number of elements, while a "set" as used herein when referring to airfoils includes any number being one or more. All directional references (e.g., radial, axial, proximal, distal, upper, lower, upward, downward, left, right, lateral, front, back, top, bottom, above, below, vertical, horizontal, clockwise, counterclockwise, upstream, downstream, forward, aft, etc.) are only used for identification purposes to aid the reader's understanding of the present disclosure, and do not create limitations, particularly as to the position, orientation, or use of aspects of the disclosure described herein. Connection references (e.g., attached, coupled, connected, and joined) are to be construed broadly and can include intermediate members between a collection of elements and relative movement between elements unless otherwise indicated. As such, connection references do not necessarily infer that two elements are directly connected and in fixed relation to one another. The exemplary drawings are for purposes of illustration only and the dimensions, positions, order, and relative sizes reflected in the drawings attached hereto can vary.

Figure 1:
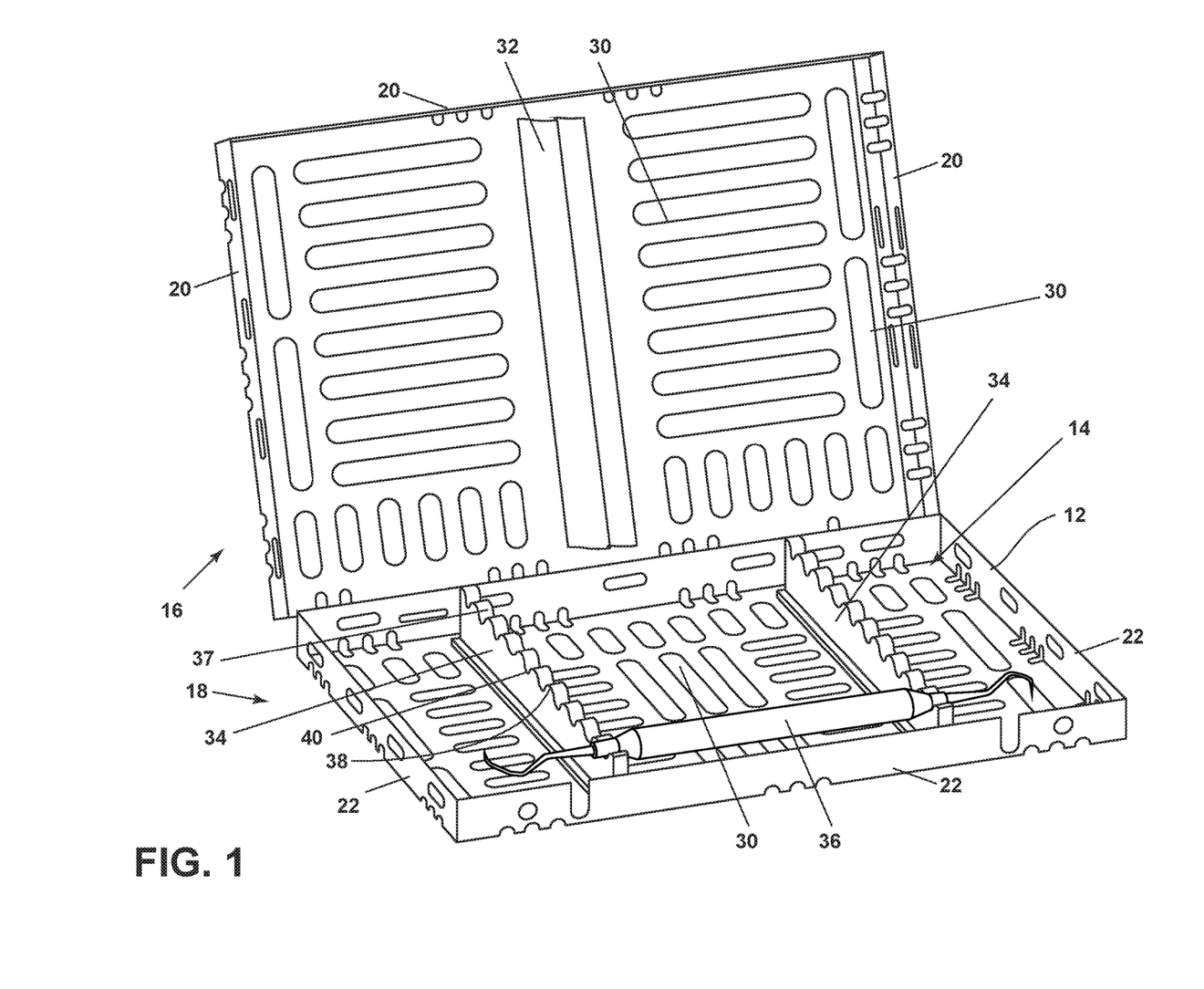
FIG. 1 is a perspective view of a cassette in an opened position, including two utensil holders having a dental tool positioned on the utensil holders.

Referring to FIG. 1, a cassette 10 includes a housing 12 defining an interior 14. The housing 12 can be made of metal, for example, while any suitable material is contemplated, preferably a material that is resistant to high temperatures and less susceptible to supporting bacteria or soil buildup, such as stainless steel, for example. The cassette 10 is shown in the opened position, having a top portion 16 and a bottom portion 18. The top portion 16 and the bottom portion 18 can be separable, such that the top portion 16 can attach to the bottom portion 18 to enclose the interior 14 in a closed position, while other organizations, such as a hinged connection between the two portions 16, 18, is contemplated. A closure, such as a latch, can be used to secure the housing 12 in the closed position. The top portion 16 can include a set of walls 20, which are adapted to overlap with a second set of walls 22 of the bottom portion 18, when the cassette 10 is in the closed position.

The cassette 10 can further include a plurality of openings 30 provided in the housing 12. The openings 30 provide for permitting a fluid or gas to enter the interior of the cassette 10 while in the closed position, in order to securely contain dental tools for cleaning, while permitting cleaning agents or liquids to enter the interior 14. The openings 30 can be provided in the top portion 16, the bottom portion 18, the walls 20, 22, or any other suitable portion of the cassette 10. In another example, the openings 30 can permit for ultrasonic cleaning of tools within the cassette 10, while other cleaning methods are contemplated, such as dedicated instrument washing machines, autoclaving, steaming or steam cleansing, heat ovens, chemical vapors, cold sterilization for heat sensitive instruments, fluid cleaning or sanitizing agents, chemistries, or any other suitable method or product.

The top portion 16 can include a tool securing insert 32. The tool securing insert 32 provides a downward force from the top portion 16 when the cassette 10 is in the closed position to hold any dental tools in place. Without this insert, the tools would fall out of place if the cassette 10 is not carried flat or may be improperly cleaned. However, the tool securing insert 32 then occupies a large portion of the space on the top wall 20, which negatively impacts capacity of the cassette 10.

Similarly, the bottom portion 18 includes a pair of tool holders 34. The tool holders 34 are spaced, such that a dental tool 36 can be lain or supported between them, and then held in place by the tool securing insert 32 when the housing 12 is in the closed position. The tool holders 34 includes a top wall 37, which includes a substantially sinusoidal profile defining a set of peaks 38 and valleys 40 between the peaks 38. The dental tool 36 can rest within the complementary valleys 40 among the spaced tool holders 34. However, the tool holders 34 are only capable of holding tools based upon the number of valleys 40, as well as being limited by the size of the valleys 40 and the cassette 10. Thus, the carrying capacity or cleaning capacity of the cassette 10 is limited by the tool holders 34 provided within the cassette 10, as opposed to the limitations of the cassette itself.

Figure 2:
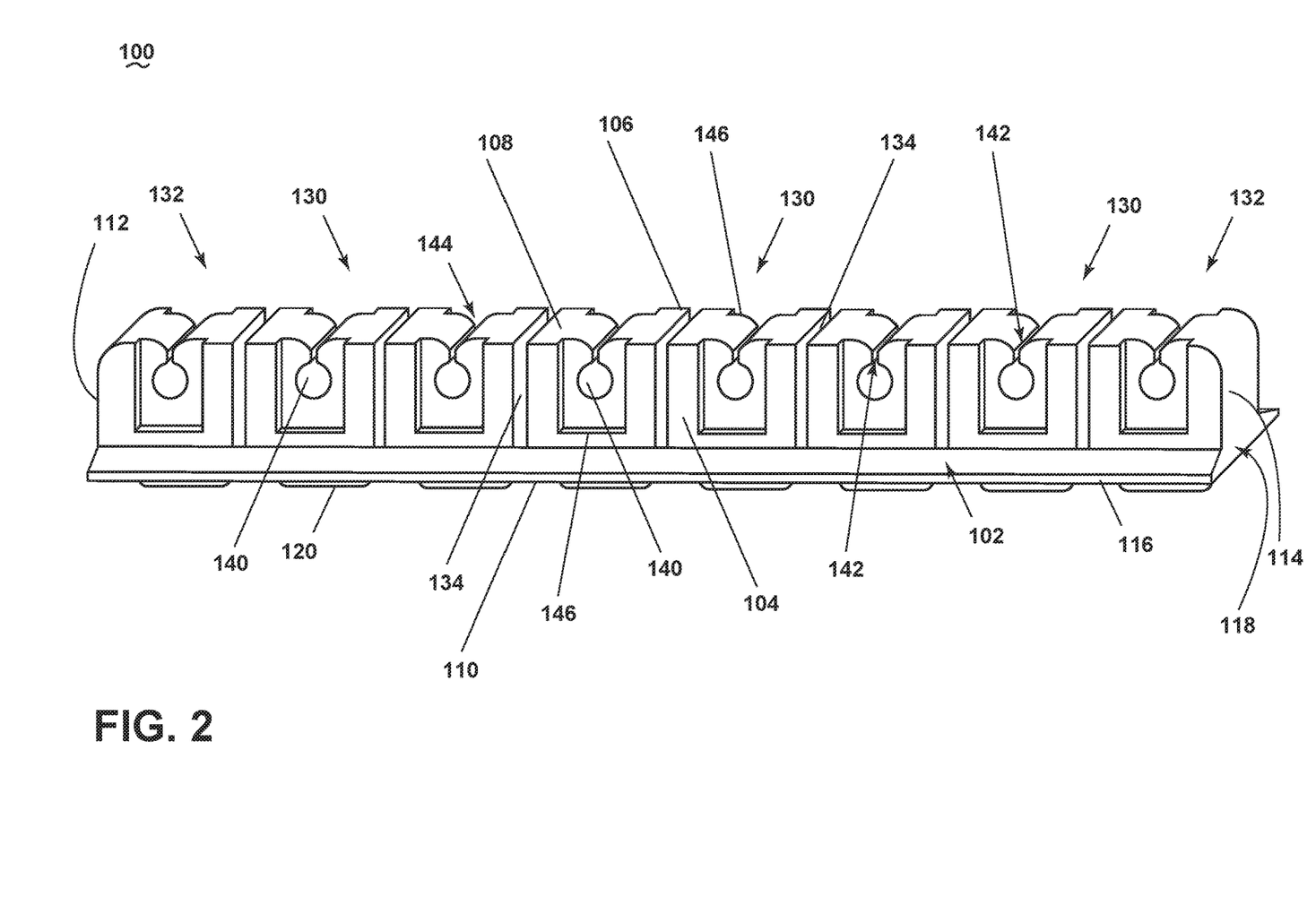
FIG. 2 is a perspective view of a dental utensil holder for use within a cassette for holding dental tools.

Referring now to FIG. 2, a dental tool holder 100 includes a body 102. The body 102 can be made of silicone, for example, while other rubber or polymeric materials are contemplated. Preferably, the material used is one that is resistant to high temperatures, such as those above the boiling point of water to permit steam or high-temperature washing and sanitizing of dental tools or instruments, while also being resistant to debris buildup or bacterial attachment or growth. Additionally, the material can be somewhat flexible, permitting flexion for inserting or removing dental tools or instruments, or inserting the dental tool holder 100 into a cassette.

The body 102 can include a front face 104 and a rear face 106, a top surface 108, and a bottom surface 110, and having opposing ends 112, 114. The body 102 can include a thickened based portion or a widened base portion 116, that has a triangular profile 118 or a truncated triangular profile, while any suitable profile is contemplated. The truncated triangular profile is advantageous, because it provides a stable, widened base, which confronts the bottom of the cassette and is held in place against a cassette by a set of feet 120. Preferably, the base portion 116 is one that is sized wide enough to include feet 120. Furthermore, it should be understood that the body 102 need not be as wide (measured between the front face 104 and the rear face 106) as shown, and can be thinner, which provides of better cleaning of dental tools or instruments carried by the dental tool holder 100, as well as reduced buildup or debris during cleaning.

A set of slots 134 can separate the body 102 into eight similar sections, with the middle six sections 130 being similar, and two opposite end sections 132 each including a curved transition between the top surface 108 and the ends 112, 114, respectively. The slot 134 can extend into the body 102, extending from the top surface 108 toward the bottom surface 110, terminating at the widened base portion 116. The slots 134 can separate and at least partially define the sections 130, 132. While shown as eight sections, it should be understood that any number of sections are contemplated, such a four, six, or eight, in non-limiting examples. The particular cassette, or size thereof, can be determinative of how large or how many sections 130, 132 can be included with particular the dental tool holder 100.

Each sections 130, 132 includes an opening 140, which connects to the top surface 108 by a slit 142. The slit 142 can be sized such that a dental tool will not pass through the slit 142 unless a user presses the dental tool to pass through the slit 142 and into the opening 140. It is further contemplated that different slits 142 can be utilized on a dental tool holder 100, adapted to different dental tools. It is also contemplated that such differentiation be identified on the dental tool holder 100, such as by color coding or indicia in non-limiting examples.

The top surface 108, adjacent to the slit 142, is curved, forming a valley 144 in the top surface 108 at each slit 142. The valley 144 can provide for guiding a tool toward the slit 142 while being inserted. The slit 142 can be sized such that a dental tool or instrument does not readily fall through or pass through the slit 142 into the opening 140, without pushing it into or pulling it from the opening 140 by a user. In this way, a dental tool or instrument can be carried within the dental tool holder 100, within the opening 140 through the slit 142. When carrying dental tools or instruments in both a top portion and a bottom portion of a cassette, the carrying capacity of the dental tool holder 100 is increased, such as being doubled without requiring additional elements to secure the tools in place. The slots 134 provide room for flexion of the sections 130, 132, such that the sections 130, 132 can flex at the slits 142 to permit a user to insert a dental tool or instrument through the slit 142 and into the respective opening 140. It should be appreciated while the valleys 144 are shown as aligned with the openings 140, alternate arrangements are contemplated, such as the valleys 144 being offset from the openings 140, and the slits 142 extending in a diagonal orientation to connect the offset valleys 144 to the openings 140. In another example, it is contemplated that a first set of tools can be provided in the openings 140, through the slits 142, and can include a second set of tools provided in the valleys 114, which can be held in place by a holder, such as the insert 32 of FIG. 1.

Each section 130, 132 also includes a recess 146 on both the front face 104 and the rear face 106, defining a reduced width measured between the front face 104 and the rear face 106. The recesses 146 provide for reduced material utilized by the dental tool holder 100, while also minimizing the surface contact between the dental tool holder 100 and the tool carried by the dental tool holder 100. The remaining thicker portions of each section, defined relative to the recesses 146, can provide for the necessary rigidity for holding any inserted tools, such that any tools do not touch one another during cleaning or use. Minimizing the surface contact can provide for improved cleaning, as well as reduced debris collection during cleaning. It should be understood that the width is not limited as shown in FIG. 2, but can be wider or thinner than that shown. Ideally, the width at the recess 146 is minimized to be as thin as possible without suffering from excessive degradation or wear from multiple cycles of use. This maximizes cleaning effectiveness, without requiring early replacement of the dental tool holders 100.

It should be appreciated that the dental tool holder 100 described herein provides for carrying more or additional dental tools or instruments for cleaning, sanitizing, or carrying instruments, even for use. This increases speed of cleaning multiple sets of tools, as well as reduces packaging or storage space required. Such benefits increase savings or reduces costs, as well as environmental impact during cleaning. Often, prepackaged sets of dental instruments may have more or less tools that are desired by the particular dentist or professional, which can be wasteful or require the dentist to utilize multiple sets of tools to ensure that the proper or preferred tools are available for use. Utilizing the dental tool holders 100 within a cassette provides for selectively arranging and cleaning dental tools for use with a greater capacity, which permits a dentist or professional to utilize only the tools they will need for the particular procedure.

Figure 3:
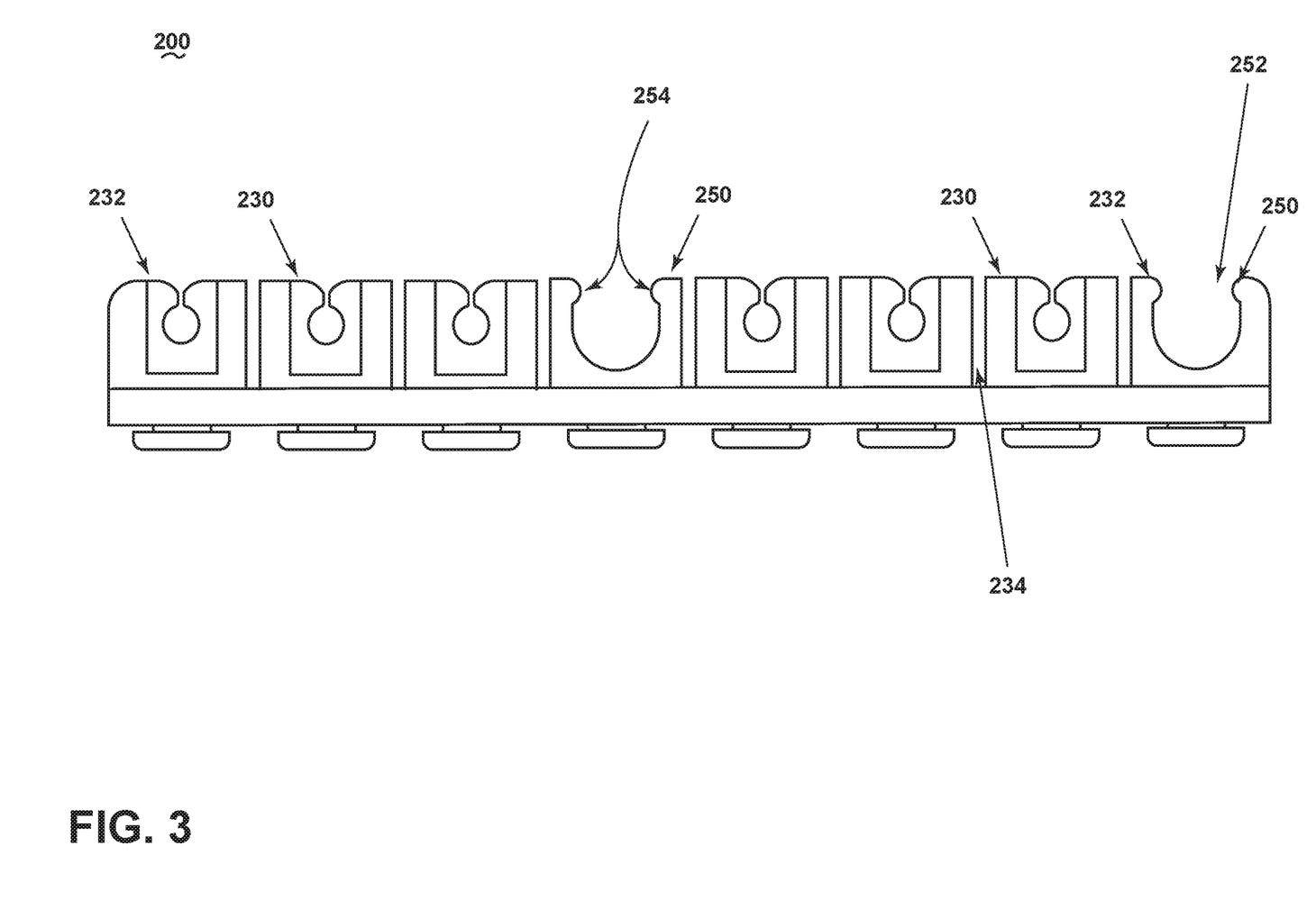
FIG. 3 is a view of another exemplary dental utensil holder for carrying different sizes or types of dental tools.

Referring to FIG. 3, another exemplary dental tool holder 200 is shown. The dental tool holder 200 can be substantially similar to that of the dental tool holder 100 of FIG. 2, with numerals being used to identify similar elements, increased by a value of one hundred, and only the differences between the two will be discussed. Therefore, while some numerals will appear in the figure, they will not be specifically addressed herein, unless they differ from that of FIG. 2. Some numerals have not been included, for brevity, but should not be considered as limiting or that any particular embodiment cannot include those items.

The dental tool holder 200 can include eight sections 230, 232, with two of the sections 250 having an enlarged or widened opening 252. The widened opening 252 can be sized to fit larger dental tools, such as electronic or functional dental tools, such as those that spin, vibrate, or pump liquid, fluid, or water, in non-limiting examples. Each widened opening 252 is further defined by a pair of opposing extensions 254 at the inlet of each opening 252. The extensions 254, provide for holding an inserted dental tool within the widened openings 252 after insertion. The extensions 254 and related sections 250 can flex into the slots 234 to permit insertion of the tool into the widened opening 252. After insertion, the section 250 and the extensions 254 can elastically return to their initial position, securing a tool within the widened opening 252. Similarly, to remove the tool for use, the user can pull the tool from the widened opening 252, and the section 250 and extensions 254 will flex again to permit removal. While not shown, it is contemplated that the section 250 with the widened opening 252 can include a recess, similar to that of FIG. 2.

When installed within a cassette, one or more of the dental tool holders 200 can be utilized, depending on the particular dental tool. For example, a dental tool that has a widened based can be inserted in the widened opening 252 of a first dental tool holder 200, while a spaced, second dental tool holder 100 can be similar to that of the one shown in FIG. 2, where the dental tool with the widened base has a thin head. Alternatively, if such a tool has a widened base and head, two of the dental tool holders 200 can be utilized within a cassette.

Figure 4:
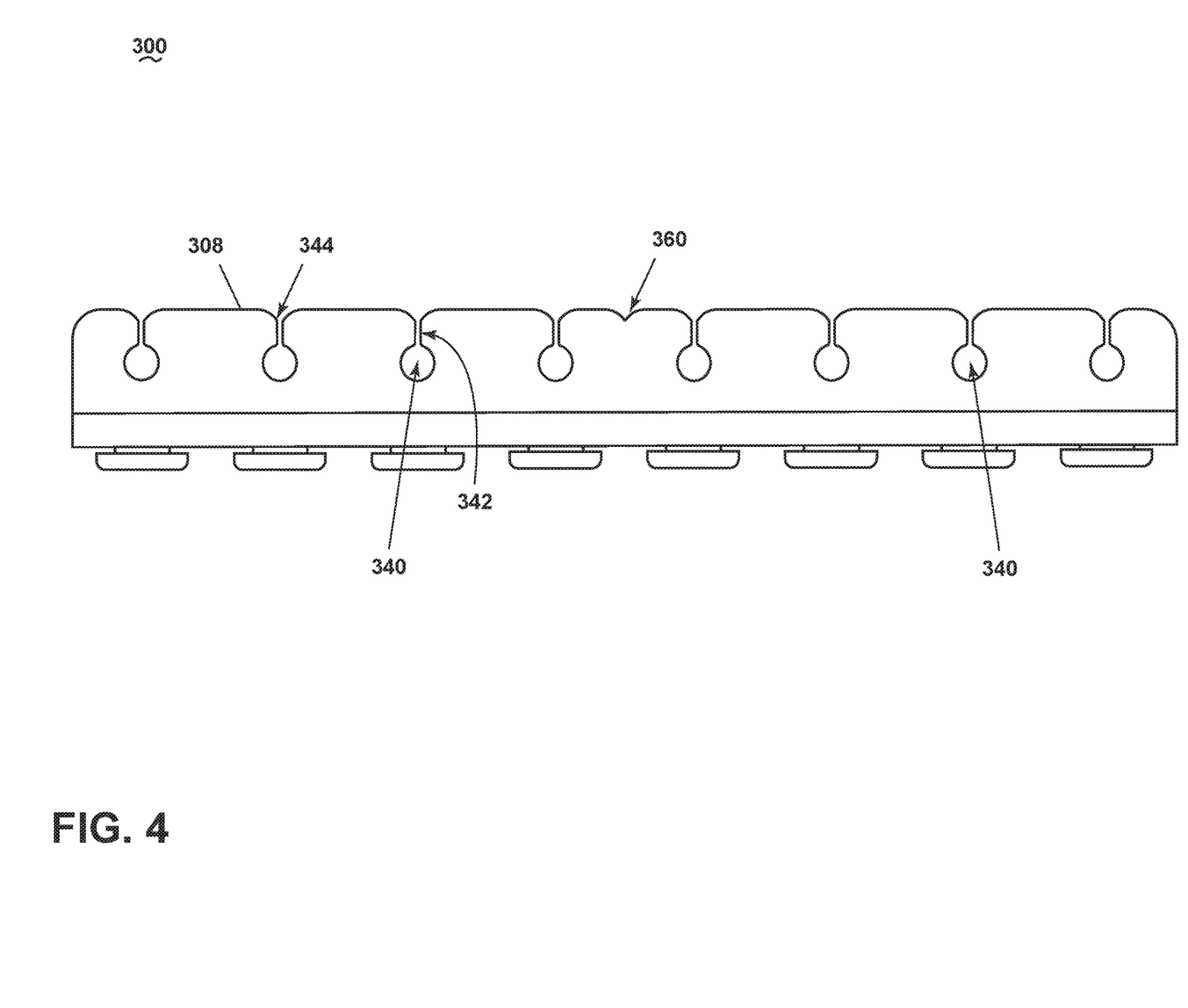
FIG. 4 is a view of another embodiment of an exemplary dental utensil holder.

Referring to FIG. 4, another exemplary dental tool holder 300 is shown. The dental tool holder 300 can be substantially similar to that of the dental tool holder 100 of FIG. 2, with numerals being used to identify similar elements, increased by a value of two hundred, and only the differences between the two will be discussed. Therefore, while some numerals will appear in the figure, they will not be specifically addressed herein, unless they differ from that of FIG. 2. Some numerals have not been included, for brevity, but should not be considered as limiting or that any particular embodiment cannot include those items which are unnumbered.

The dental tool holder 300 includes a set of openings 340, each of which are connected to the top surface 308 via a slit 342. Additionally, each slit 342 can have a valley 344 for holding a second tool above a first tool held in the openings 340. Similarly, extra or auxiliary valleys 360 can be included, unaligned with the other valleys 344 or the slits 342, and spaced from the slits 342. In this way, the capacity of the dental tool holder 300 is further increased, and is not limited by the number of openings 340 or valleys 344. While only a single auxiliary valley 360 is shown, it should be appreciated that any number of auxiliary valleys 360 can be included, and need not be arranged in the middle of the dental tool holder 300, or evenly spaced between openings 340, and can have any suitable arrangement or organization.

Figure 5:
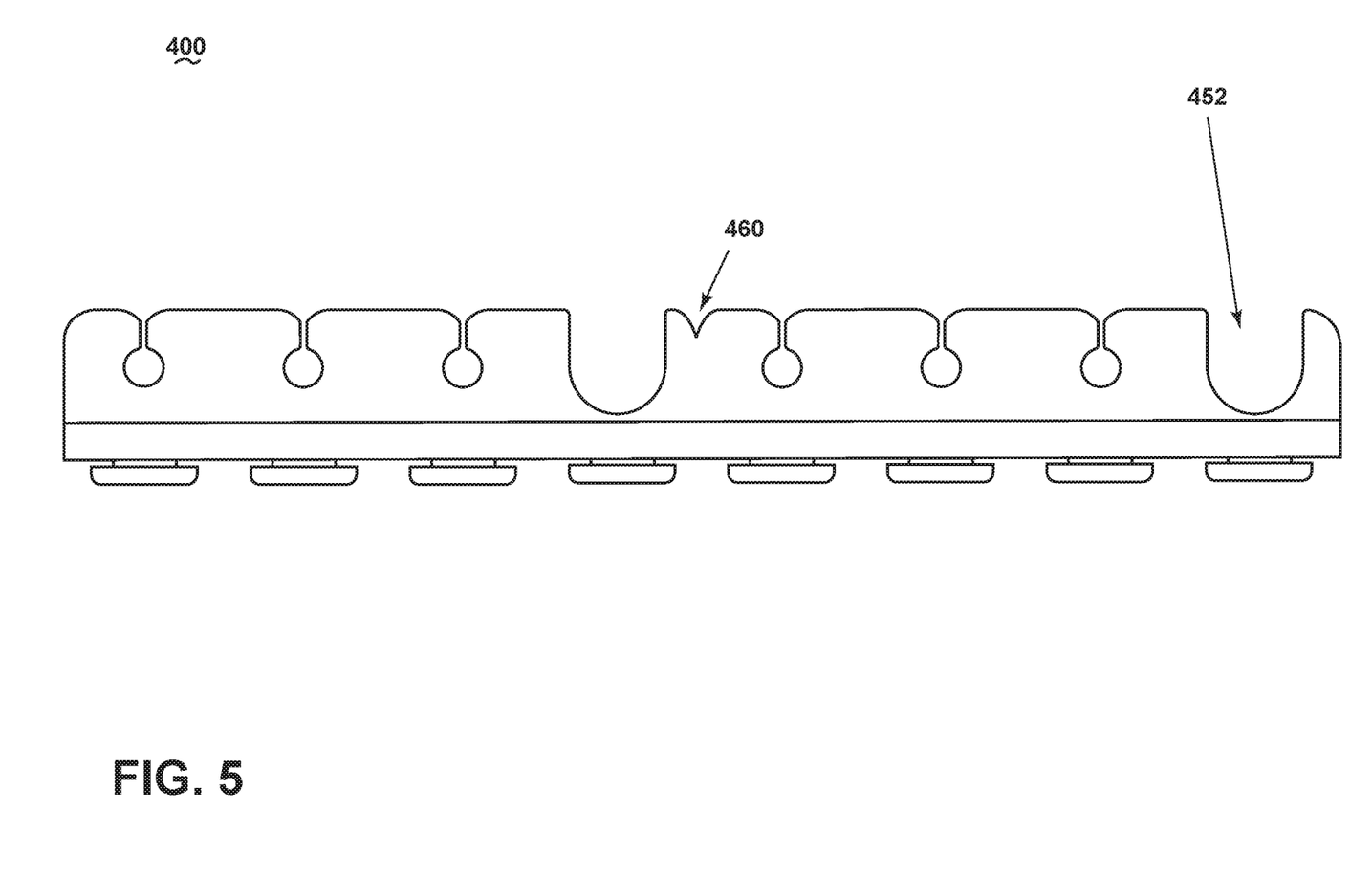
FIG. 5 is a view of yet another embodiment of a dental utensil holder, shown as two different versions.

Referring to FIG. 5, another exemplary dental tool holder 400 is shown. The dental tool holder 400 can be substantially similar to that of the dental tool holder 300 of FIG. 4, except that two openings have been replaced with widened openings 452, without the extensions 254 of FIG. 3. An auxiliary valley 460 is provided adjacent to one of the widened openings 452, while any position for the auxiliary valley 460 is contemplated.

Figure 6:
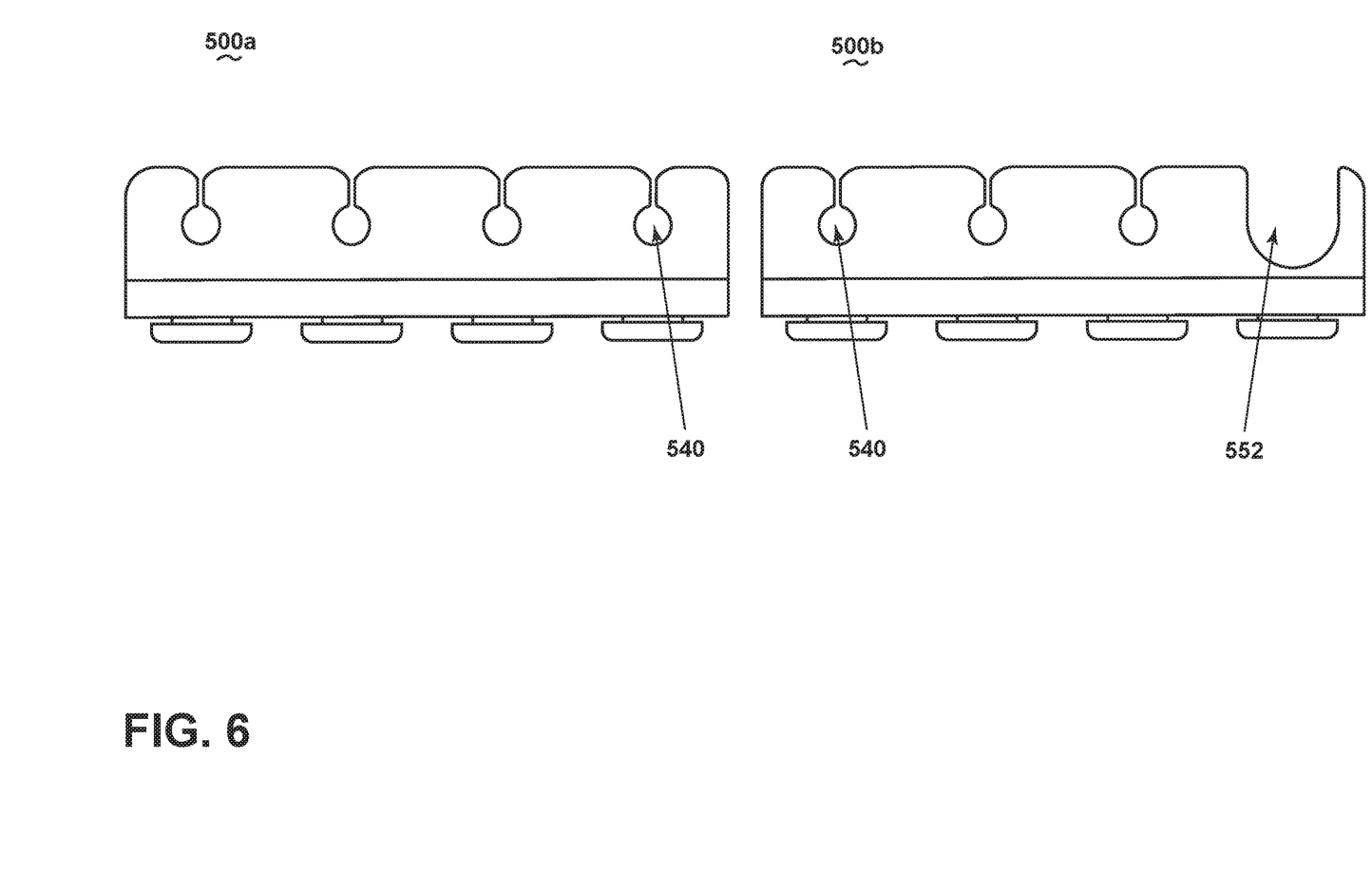
FIG. 6 is a view of still another dental utensil holder, according to an embodiment of the invention.

Referring to FIG. 6, two additional exemplary dental tool holders 500a, 500b are shown. The dental tool holders 500a, 500b can be substantially similar to that as described in FIG. 3, except that each dental tool holder 500a, 500b includes four openings, as opposed to eight as shown previously. It should be appreciated that the number of openings are not limited as shown in the drawings, but can include any number, being one or greater. The first dental tool holder 500a includes four standard openings 540, while the second dental tool holder 500b includes a widened opening 552, in addition to three standard openings 540. In this way, it should be appreciated that the dental tool holders 500a, 500b can be mixed and matched, or rearranged, to accommodate any set of dental tools, whether standardized or particular to one dentist or professional.

Figure 7:
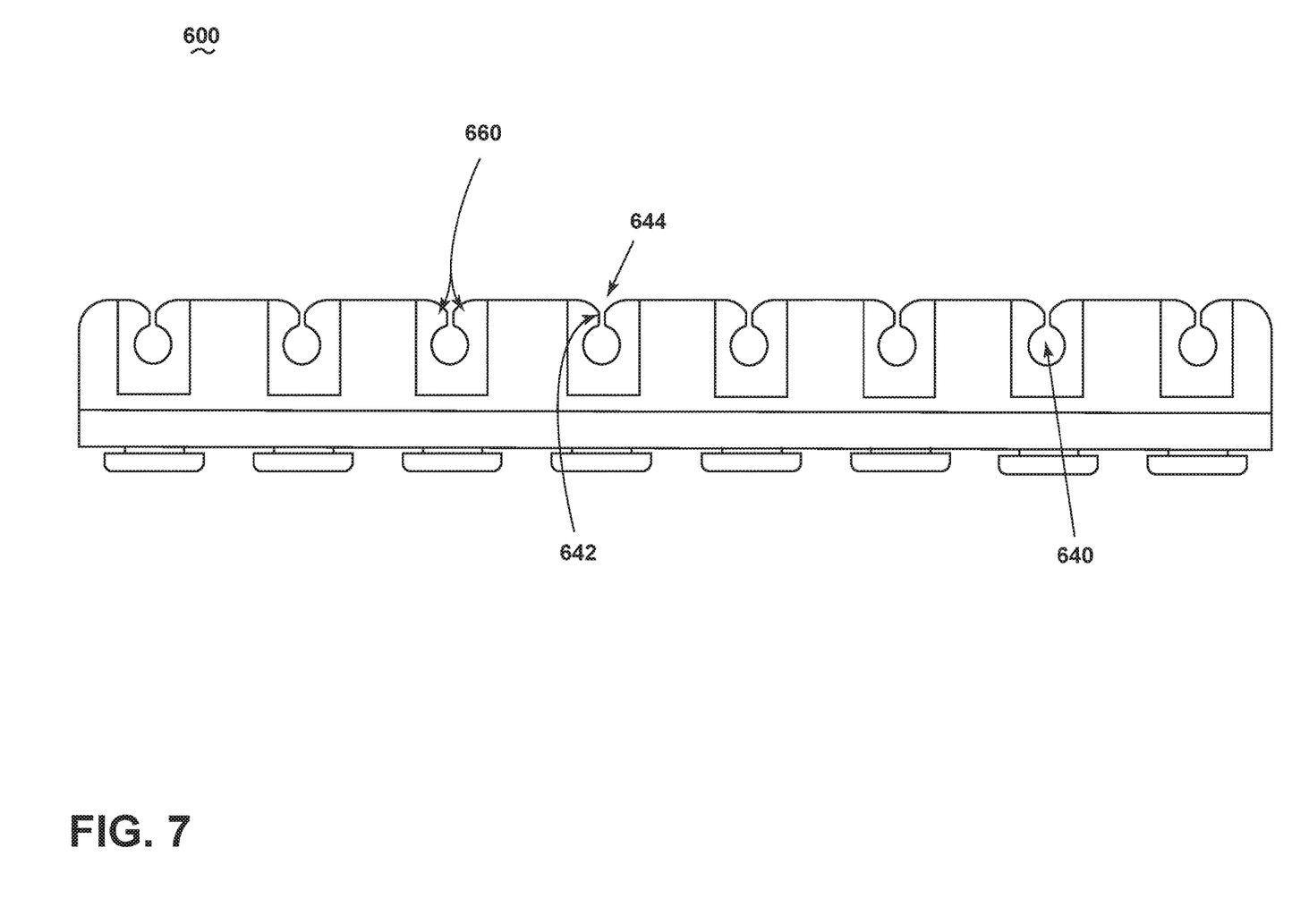
FIG. 7 is another view of yet another embodiment of a dental utensil holder.

Referring to FIG. 7, yet another exemplary dental tool holder 600 is shown. This dental tool holder 600 can be substantially similar to the dental tool holder 100 of FIG. 2, except that the slots 134 (shown in FIG. 2) have been removed. In such an example, the material for the dental tool holder 600 can be less rigid, permitting a user to insert a dental tool into the openings 640 without requiring significant flexion of the dental tool holder 600. It is further contemplated that the sizing, shaping, material composition, or spacing of dental tool holder 600 at the extensions 660, defining a slit 642, can be such that a user is permitted to push a tool through the slit 642, into an opening 640, with a valley 644 formed at the slit.

It should be appreciated that removing the slots from the dental tool holder 600 can provide for improved stability, rigidity, as well as lifetime, as compared to a dental tool holder that utilizes slots between tool-holding portions, such as sections 130, 132 of FIG. 2, for example. However, it should be understood that the tool of FIG. 2 will not necessarily suffer from these deficiencies due to the use of the slots 134.

To the extent not already described, the different features and structures of the various embodiments can be used in combination, or in substitution with each other as desired. That one feature is not illustrated in all of the embodiments is not meant to be construed that it cannot be so illustrated, but is done for brevity of description. Thus, the various features of the different embodiments can be mixed and matched as desired to form new embodiments, whether or not the new embodiments are expressly described. All combinations or permutations of features described herein are covered by this disclosure.

This written description uses examples to describe aspects of the disclosure described herein, including the best mode, and also to enable any person skilled in the art to practice aspects of the disclosure, including making and using any devices or systems and performing any incorporated methods. The patentable scope of aspects of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A tool holder for holding dental instruments, the tool holder comprising:
   a body including a front face, a rear face, and a top surface;
   a set of openings extending through the body from the front face to the rear face;
   at least one slit extending into the body from the top surface and terminating at the opening; and
   a set of slots with a slot provided between adjacent openings of the set of openings.

2. The tool holder of claim 1 further comprising at least one valley provided in the top surface, wherein the at least one valley is aligned with the at least one slit.

3. The tool holder of claim 2 further comprising at least one additional valley, wherein the at least one additional valley is unaligned with the at least one slit.

4. The tool holder of claim 1 wherein the at least one opening includes eight openings, and the at least one slit includes eight slits, with each slit terminating at one complementary opening.

5. The tool holder of claim 1 wherein a first recess is defined in the front face and a second recess is defined in the rear face.

6. The tool holder of claim 5 wherein a length of the openings, measured between the front face and the rear face, is defined by the first recess and the second recess.

7. The tool holder of claim 5 wherein the first recess and the second recess define a thin portion for the body.

8. The tool holder of claim 1 wherein the body further includes a thickened portion, defined adjacent to a bottom surface, opposite of the top surface.

9. The tool holder of claim 8 wherein the thickened portion includes a truncated triangular profile.

10. The tool holder of claim 1 further including at least one enlarged opening, such that the at least one enlarged opening is larger than that of the at least one opening.

11. The tool holder of claim 10 wherein the at least one enlarged opening includes an inlet defined by a pair of opposing extensions.

12. A tool holder assembly for holding dental instruments within a dental cassette, the tool holder assembly comprising:
    a first dental tool holder and a second dental tool holder, each including:
       a body with a set of openings, and including a set of slits complementary to the set of openings, each slit of the set of slits extending through the body to one opening of the set of openings, and
       a set of slots, with one slot of the set of slots provided between adjacent openings of the set of openings.

13. The tool holder assembly of claim 12 wherein the set of openings includes at least one enlarged opening, larger than the other openings of the set of openings, with the at least one enlarged opening including an inlet defined by a set of extensions.

* * * * *